United States Patent [19]
Aggarwal et al.

[11] Patent Number: 5,457,129
[45] Date of Patent: Oct. 10, 1995

[54] INHIBITION OF NITRIC OXIDE PRODUCTION BY RETINOIC ACID

[75] Inventors: Bharat B. Aggarwal; Kapil Mehta, both of Houston, Tex.

[73] Assignee: Research Development Foundation, Carson City, Nev.

[21] Appl. No.: 61,471

[22] Filed: May 17, 1993

[51] Int. Cl.$^6$ .................................................. A61K 31/19
[52] U.S. Cl. ...................... 514/557; 514/825; 514/895; 514/903
[58] Field of Search ...................... 514/168, 169, 514/825, 895, 903, 557

[56] References Cited

U.S. PATENT DOCUMENTS 5,157,046  10/1992  Van Wauwe et al. ............... 514/168
5,264,578  11/1993  Chandraratna ........................ 546/269

OTHER PUBLICATIONS

Chemical Abstracts (114: 79814x) 1991.

*Primary Examiner*—Raymond Kenley, III
*Assistant Examiner*—K. E. Weddington
*Attorney, Agent, or Firm*—Benjamin Aaron Adler

[57] ABSTRACT

A novel method of inhibiting production of two important mediators of cellular function, tumor necrosis factor and nitric oxide, and treating a pathophysiological state characterized by an undesirable production or level of tumor necrosis factor or nitric acid. The methods of the present invention employ retinoic acid compounds. The most preferred retinoic acid is all-trans-retinoic acid.

9 Claims, 6 Drawing Sheets

INHIBITION OF NITRIC OXIDE PRODUCTION BY RETINOIC ACID

BACKGROUND OF THE INVENTION

1. Field of the Invention

The present invention relates generally to the fields of immunology and the biochemistry of biological response modifiers. More specifically, the present invention relates to a novel method for the inhibition of tumor necrosis factor and nitric oxide production.

2. Description of the Related Art

For more than 50 years, retinoids (natural and synthetic analogues of vitamin A) have attracted great attention by researchers in dermatology, cancer research, and embryonal development. A principal biological effect of the retinoids is to inhibit the growth and/or induce differentiation of the target cells. However, the mechanism of action of retinoids in producing these biological effects is not well understood.

Macrophages play many roles in diverse physiological processes. Depending on the signal received, mononuclear phagocytes can differentiate and become competent to perform specific sets of functions. An appropriate balance between activation (stimulation) and suppression of macrophage functions is essential. For example, inappropriate regulation of activation, by virtue of excess stimulation or insufficient suppression, can lead to extensive tissue injury and damage. This tissue damage, at times, may be so destructive that the survival of the host is threatened. Sites of inflammation, containing mononuclear phagocytes, frequently exhibit extensive damage to normal cells and tissue. In addition, the mechanisms by which macrophages injure and destroy the replicating cells of microbial or neoplastic origin, can also be turned against host cells. Many of the observed biological responses to invasive stimuli, triggered by infectious or neoplastic diseases, are mediated by host-secreted cytokines, in particular, the secreted products of activated macrophages.

Retinoids have been shown by several investigators to modulate the growth and differentiation functions of mononuclear phagocytes. For example, ATRA has been shown to downregulate the production of interferon by phytohaemagglutinin or anti-thymocyte globulin stimulated lymphocytes. Both IL-1 and IL-3 production was induced in vitro in human peripheral blood mononuclear cells and murine WEHI-3 cell lines, respectively, in the presence of retinoic acid in a dose-dependent manner. More recently, an augmenting effect of retinoic acid and 13-cis retinoic acid on IL-1 production by murine keratinoyctes was observed. Induction of IL-1 receptors in EL-4 cells and IL-2 receptors on activated human thymocytes was observed following the culture of these cells in presence of retinoic acid. Furthermore, transforming growth factor (TGF-$\beta_1$) protein as well its receptor can both be induced in HL-60 (promyelocytic leukemia) cells following their differentiation with retinoids. On the other hand, retinoic acid has been shown to down modulate the transcription of epidermal growth factor-receptor in human epidermoid carcinoma ME180 cells. Similarly, high concentrations of ATRA inhibit the production of interferon by L-929 cells infected with New Castle-disease virus.

Tumor necrosis factor-$\alpha$ (TNF) has been implicated as an important mediator of the inflammatory response. Nitric oxide (NO—), a highly reactive flee-radical produced by the activated macrophages, has emerged as another important mediator of inflammatory responses. TNF in combination with NO— and/or other cytokines (such as interleukin-1 and interleukin-6) may bring about the tissue destruction observed in certain autoimmune diseases such as psoriasis, rheumatoid arthritis, osteoarthritis and other joint diseases.

The prior art remains deficient in the lack of effective methods of inhibiting the production of tumor necrosis factor and nitric oxide. Moreover, the prior art is deficient in the lack of an effective method to treat pathophysiological states characterized by undesirable levels of tumor necrosis factor or nitric oxide in the body.

SUMMARY OF THE INVENTION

It is, therefore, an object of the present invention to provide a novel method of inhibiting the production of tumor necrosis factor.

A further object of the present invention is to provide a novel method for inhibiting nitric oxide.

Yet another object of the present invention is to provide a novel and effective method for treating pathophysiological states characterized by an undesirable level of tumor necrosis factor or nitric oxide in the body.

In order to achieve the above objects, there is provided one embodiment of the present invention, a method of inhibiting the production of tumor necrosis factor comprising the step of administering to an animal a pharmacologically effective dose of a retinoic acid compound.

In another embodiment of the present invention, there is provided a method of inhibiting the production of nitric oxide comprising the step of administering to an animal a pharmacologically effective dose of a retinoic acid compound.

In yet another embodiment of the present invention, there is provided a method of treating a pathophysiological state in an animal, wherein said state is characterized by production of an undesirable level of tumor necrosis factor, comprising the step of administering a pharmacologically effective dose of a retinoic acid compound.

In still yet another embodiment of the present invention, there is provided a method of treating a pathophysiological state in an animal, wherein said state is characterized by production of an undesirable level of nitric oxide, comprising the step of administering a pharmacologically effective dose of a retinoic acid compound.

The present invention illustrates the effect of various retinoids on two important mediators of inflammation: TNF and NO— production. The results obtained suggest that all-trans retionic acid (ATRA) was most potent of all the retinoids studied and at physiological and pharmacologically achievable dose levels (0.1–1.0 $\mu$M), it inhibited both the TNF and NO— production by activated murine macrophages.

Other and further objects, features and advantages will be apparent from the following descriptions of the presently preferred embodiments in the invention which are given for the purpose of disclosure and when taken in conjunction with the accompanying drawings.

BRIEF DESCRIPTION OF THE DRAWINGS

The drawings are not necessarily to scale. Certain features of the invention may be exaggerated in scale or shown in schematic form in the interest of clarity and conciseness.

DETAILED DESCRIPTION OF THE INVENTION

Figure 1:
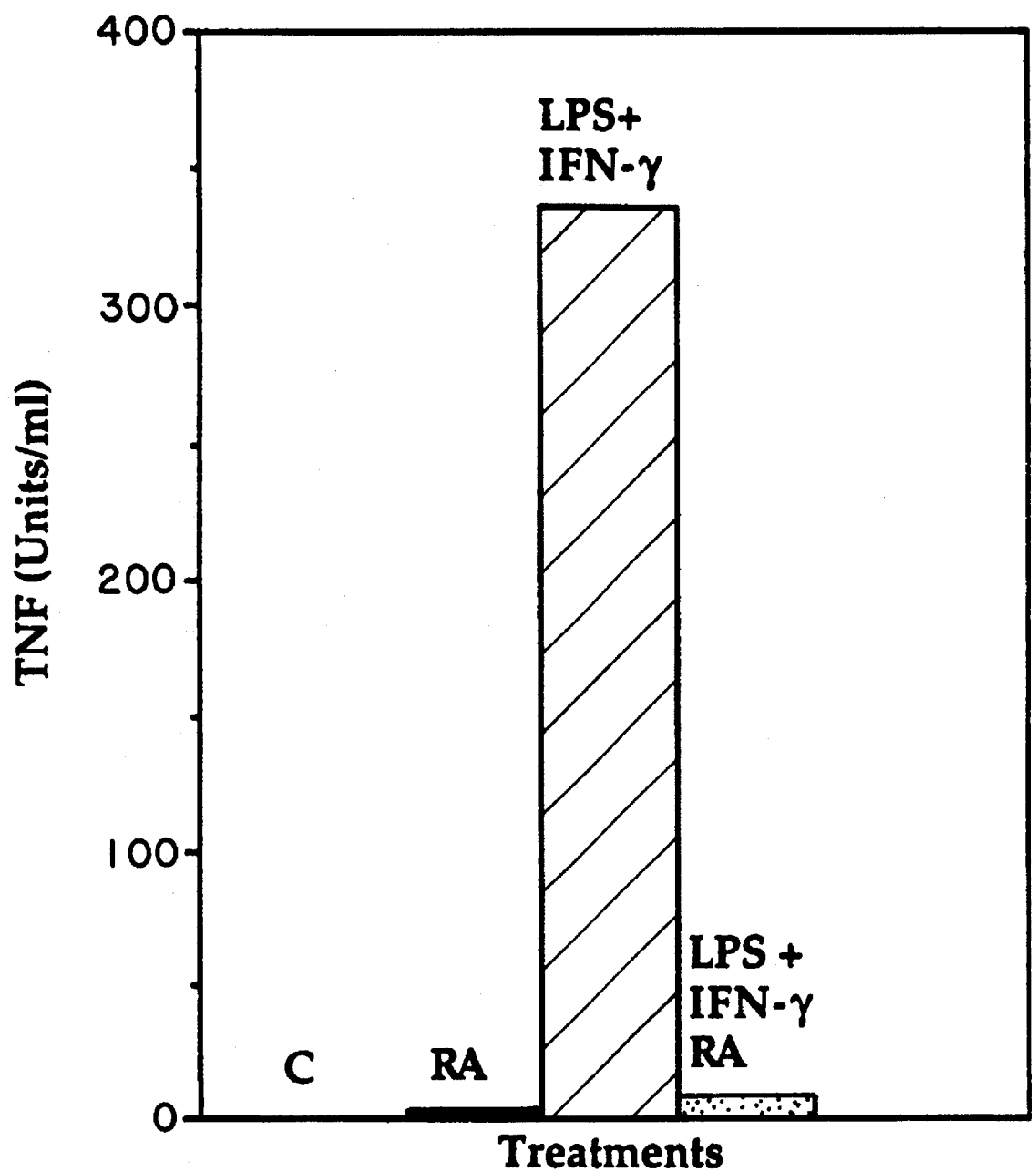
FIG. 1 shows the effect of in vitro all-trans retinoic acid (ATRA) treatment on TNF release by activated murine peritoneal macrophages. Two million macrophages were activated in 24-well plates with Interferon-g (IFN-g) (10 U/ml) and lipopolysaccharide (LPS) (100 ng/ml) in the presence or absence of ATRA (1 µM). Four hours later, cell-free supernatants were harvested and assayed for TNF activity as described in Example 1. The results shown represent one of four similar experiments.

The present invention provides a method of inhibiting the production of tumor necrosis factor comprising the step of administering to an animal a pharmacologically effective dose of a retinoic acid compound. The present invention also provides a method of inhibiting the production of nitric oxide comprising the step of administering to an animal a pharmacologically effective dose of a retinoic acid compound.

In addition, the present invention also provides a method of treating a pathophysiological state in an animal, wherein said state is characterized by production of an undesirable level of tumor necrosis factor, comprising the step of administering a pharmacologically effective dose of a retinoic acid compound. Similarly, the present invention also provides a method of treating a pathophysiological state in an animal, wherein said state is characterized by production of an undesirable level of nitric oxide, comprising the step of administering a pharmacologically effective dose of a retinoic acid compound.

Generally, any retinoic acid compound which inhibits the production of tumor necrosis factor is useful in the methods of the present invention. More preferably, the retinoic acid compound is selected from the group consisting of all-trans-retinoic acid, 4-hydroxy-retinoic acid and 13-cis-retinoic acid. Most preferably, the retinoic acid compound is all-trans-retinoic acid.

The methods of the present invention may be administered to any animal. Most preferably, the retinoic acid compounds useful in the methods of the present invention are administered to a human.

Generally, the dose of the retinoic acid compound given in the methods of the present invention is any that inhibits the production of tumor necrosis factor or nitric oxide in the animal. More preferably, the dose of the retinoic acid compound is between 10 nM and 1 µM.

Generally, the methods of treating a pathophysiological state of the present invention may be useful for any disease characterized by an undesirable level of tumor necrosis factor or nitric oxide production. Preferably, these methods are selected from the group consisting of sepsis, cachexia, neoplastic diseases such as Karposi's sarcoma, cerebral malaria, capillary leak syndrome .and autoimmune disease. Representative autoimmune diseases include systemic lupus erythematosus, rheumatoid arthritis and multiple sclerosis. In addition, the methods of the present invention may be useful in the treatment of transplant rejection in humans.

The elevated levels of serum TNF in the circulation has been observed only under pathological conditions including bacterial, viral or parasitic infections, fever, cancer, autoimmune disorders, septic shock or under inflammatory conditions. The levels of TNF in serum may vary considerably based on the site of production and method of its determination. Since there are two different forms of TNF, i.e., membrane-associated form (molecular weight 26 kDa) and secreted form (molecular weight 17 kDa), the serum samples can determine only the latter form. The membrane-bound TNF is difficult to detect and requires histological or flow cytometric examination of the tissue. Thus the relevance of the circulating serum TNF concentrations in most pathological conditions has been questioned. The detection or lack of detection of circulating serum levels of TNF may not be adequate.

In most instances when TNF is secreted in the circulation, there is also a production of TNF inhibitor which is a soluble form of the TNF receptor. This inhibitor usually blocks the biological activity of TNF. Therefore, the determination of TNF levels by bioassay do not provide the true estimation of the levels of the cytokine. In most instances, immunoassays specific for TNF can be useful in circumventing this problem. Thus, the methods of the present invention to treat any of the above-mentioned pathophysiological states may be accomplished without an exact determination of the serum levels of TNF.

The dosage administered is dependent upon the age, weight, kind of concurrent treatment, if any, and nature of the pathophysiological state. The effective composition useful in the methods of the present invention may be employed in such forms as capsules, tablets, liposome encapsulations, liquid solutions, suspensions or elixirs for oral administration or sterile liquid forms such as solutions, suspensions or emulsions. Any inert carrier is preferably used, such as saline or phosphate buffered saline or any such carrier in which the compounds used in the methods of the present invention have suitable solubility properties.

The retinoic acid compounds useful in methods of the present invention may be administered in a pharmaceutically acceptable carrier. The pharmaceutically acceptable carrier is any solvent with which the retinoic acid compound is compatible and which is non-toxic to the individuals treated at the amounts administered. A pharmacological dose of the retinoic acid compound useful in the methods of the present invention is that amount which inhibits the production of tumor necrosis factor or nitric oxide.

The cell lines L-929 (Mouse connective tissue) and RAW 264.7 (murine macrophage) were obtained from American Type Culture Collection (Rockville, Md.). The cell lines tested negative for mycoplasma. The media and serum were screened for endotoxin by Limulus amebocyte lysate assay and were found to contain less than 0.25 ng/ml.

The following examples are given for the purpose of illustrating various embodiments of the methods of the present invention and are not meant to limit the present invention in any fashion.

EXAMPLE 1

Cell culture

Murine L-929 and RAW 264.7 cell cultures were maintained in continuous exponential growth by weekly passages. Both cell lines were routinely grown in RPMI 1640 medium supplemented with glutamine (2 mM), 10% fetal calf serum, 10 mM Hepes buffer, and antibiotics (penicillin 100 U/ml and streptomycin 100 µg/ml) in a humidified incubator in 5% $CO_2$ in air.

EXAMPLE 2

Isolation of mouse macrophages

Resident peritoneal macrophages were obtained from mice by peritoneal lavage, using 5 ml ice-cold Dulbecco's phosphate buffered saline containing gentamicin (40 µg/ml) as described by Mehta et al., *J. Immunol.*, 136:4206–4212 (1986). Briefly, pooled cells were sedimented at 400 x g for 10 minutes and were resuspended in medium to a concentration of $1.5 \times 10^6$/ml. One milliliter samples of the cell suspension were added per well to 2 $cm^2$ flat bottomed well tissue culture plates. The cells were incubated for 60 minutes at 37° C. in a 5% $CO_2$ air incubator. Nonadherent cells were removed by washing vigorously three time with warmed medium. Adherent cells ($10^6$ cells/2 ml/well in 24-well plates) thus obtained were judged to be more than 95% macrophages by phagocytic uptake and nonspecific esterase staining.

During the exponential growth phase, RAW-264.7 cells were stimulated with the reagents indicated, in wells of a 24-well plate ($2 \times 10^6$ at 2 ml). At indicated time intervals, the cell-free supernatants were harvested and an aliquot was used immediately for TNF and NO— determinations. A separate aliquot was stored at −80° C. for later use to determine the TNF protein using a murine TNF-ELISA kit.

EXAMPLE 3

Determination of TNF in culture supernatants

The cytotoxicity assays were carried out with $20 \times 10^3$ cells treated with actinomycin D (1 µg/ml) along with TNF for 24 hours. For this, cells were plated for overnight in 0.1 ml of the medium in 96-well Falcon plates. Thereafter, the medium was removed and a serial dilution of human TNF or assay supernatants was layered in 0.1 ml of the volume. After 24 hours of incubation at 37° C., the medium was removed and viable cells were monitored by crystal violet staining according to the procedure described by Leu et al. *J. Immunol* 147:1816 (1991). The percent of relative cell viability was calculated as optical density in the presence of test sample divided by optical density in the absence of test sample medium multiplied by 100. Murine TNF was measured from culture supernatants using a high sensitivity ELISA. Briefly cells were stained with 0.5% crystal violet in 20% methanol for 15 minutes at room temperature. Excess stain was removed under tap water and the plate was air dried. Stained cells were solubilized with Sorenson's buffer (0.1M sodium citrate in 5% ethanol, pH 4.2) and the absorbance of the solubilized dye was read at 540 nm on a Dynatech MR 5000 microplate reader. The percent relative cell viability was calculated as optical density in the presence of test sample divided by that of with the medium multiplied by 100.

Inhibitors of TNF activity can mask its activity. This can lead to underestimation of TNF by bioassays. Therefore, the ELISA assay (R & D System Inc.) was employed for the determination of TNF. This assay is highly quantitative, sensitive (sensitivity in picogram range) and specific. It employs the quantitative "sandwich" enzyme immunoassay technique. A monoclonal antibody specific for TNF was coated onto the microtiter plate for overnight. Then the samples were pipetted into the wells and the cytokine, if any, was captured by the immobilized antibody. After washing away any unbound sample proteins, an enzyme-linked polyclonal antibody specific for TNF was added to the wells and allowed to bind the cytokine bound during the first incubation. Following a wash to remove any unbound antibody-enzyme reagent, a substrate solution was added to the wells and color developed in proportion to the amount of cytokine bound in the initial step. Along with the samples to be tested, a series of wells were prepared using known concentrations of the TNF standards. A curve plotting the optical density versus the concentration of cytokine in these standard wells was prepared. By comparing the optical density of the samples to this standard curve, the concentration of the cytokine in the unknown samples is then calculated.

EXAMPLE 4

Measurement of nitric oxide

The amount of stable nitrite, the end product of nitric oxide generation by activated macrophages under different conditions, was determined by the method of Ding et al. *J. Immunol.* 145:940 (1990). Briefly, 50 µl of culture supernatant from control or LPS (100 ng/ml) and/or IFN-γ(10 U/ML)-stimulated macrophages alone or cultured in presence of ATRA or supernatants from cell lines stimulated with phorbol myristic acetate (PMA, 20 ng/ml) were mixed with an equal volume of Griess reagent (1% sulfanilamide; 0.1% naphthylethylene diamine dihydrochloride; 2.5% $H_3PO_4$) at room temperature for 10 minutes. The absorbance at 550 nm was determined on a Vmax microplate reader. Nitrite in each test sample was determined by extrapolation from a sodium nitrite standard curve in each experiment.

EXAMPLE 5

Measurement of Transglutaminase assay

Transglutaminase activity in cell lysates was assayed by determining $Ca^{+2}$-dependent incorporation of tritiated-putrescine into dimethyl-casein at 37° C. as detailed by Mehta et al., (1986). Briefly, cells were washed three times in isotonic saline and were scraped from the dish in a minimal volume of 20 mM Tris-HCl, pH 7.6 containing 150 mM NaCl, 1 mM EDTA and 15 mM β-mercaptoethanol and were lysed by sonication. Tissue TGase activity in cell lysate was determined at 37° C. in a final volume of 100/μl reaction mixture containing 50 mM Tris-HCl, pH 7.5, 30 mM NaCl, 2 mg/ml N,N'-dimethylcasein, 10 mM dithiothreitol, 5 mM $CaCl_2$, 0.2 mM putrescine and 0.4 mM $^3H$ putrescine (specific activity 33.1 Ci/mmole). The enzyme activity was expressed as nanomoles of putrescine covalently incorporated into dimethylcasein per hour per milligram of cell protein. Protein content in cell extracts was determined by Biorad's Bradford reagent.

EXAMPLE 6

Effects of ATRA on TNF production

FIG. 1 demonstrates that LPS (100 ng/ml) in combination with IFN-γ ((10 U/ml) induces high TNF production in murine resident peritoneal macrophages as determined in a biological assay using L929 as target cells. The cytotoxic ability of culture supernatants from activated macrophages could be completely abolished by concomitant addition of a monospecific antibody against TNF during incubation with L929 cells. Co-culture of cells with ATRA during the activation phase resulted in a significant inhibition of TNF release. ATRA was most potent inhibitor of TNF production by activated macrophages, whereas retinaldehyde was completely inactive (Table 1). Other analogs of vitamin A inhibited TNF production in the following order: ATRA>4-hydroxy ATRA>13-cis retinoic acid>retinol (vitamin A)>retinaldehyde (Table 1).

TABLE 1

Effect of Retinoic acid and its analogues on the LPS and IFN-g-dependent induction of Transgutaminase and TNF from murine peritoneal macrophages

| Treatment | Transglutaminase (cpm/μg/hour) | TNF (units/ml) |
| --- | --- | --- |
| None | 165 + 0 | not detectable |
| IFN-g + LPS | 291 + 0 | 54 + 14 |
| ATRA | 934 + 25 | 0.9 + 0.1 |
| 13 cis-RA | 1014 + 60 | 35 + 1.4 |
| Retinal | 184 + 7 | 46 + 2.8 |
| Retinaldehyde | 518 + 0.16 | 54 + 14 |
| 4-OH-ATRA | 1108 + 10 | 29 + 1.4 |
| Vitamin $D_3$ | 368 + 0 | 46 + 8 |

The ATRA-induced inhibitory effect on TNF production was a specific effect and not due to non-specific toxicity of the drug to the cells. Macrophages treated with ATRA showed no appreciable change in their morphology when compared to untreated control cells. Expression of transglutaminase, an enzyme that is specifically induced by ATRA in cultured macrophages, was elevated in presence of ATRA and other analogs (Table 1). DMSO, the vehicle used for delivering ATRA to the cultures, had no effect alone on TNF production by the activated macrophages. Moreover, addition of ATRA or DMSO to L929 cell cultures did not affect the ability of exogenously added TNF to kill these cells. ATRA-mediated suppression of TNF production by activated macrophages was dose-dependent and time-dependent.

Figure 2A:
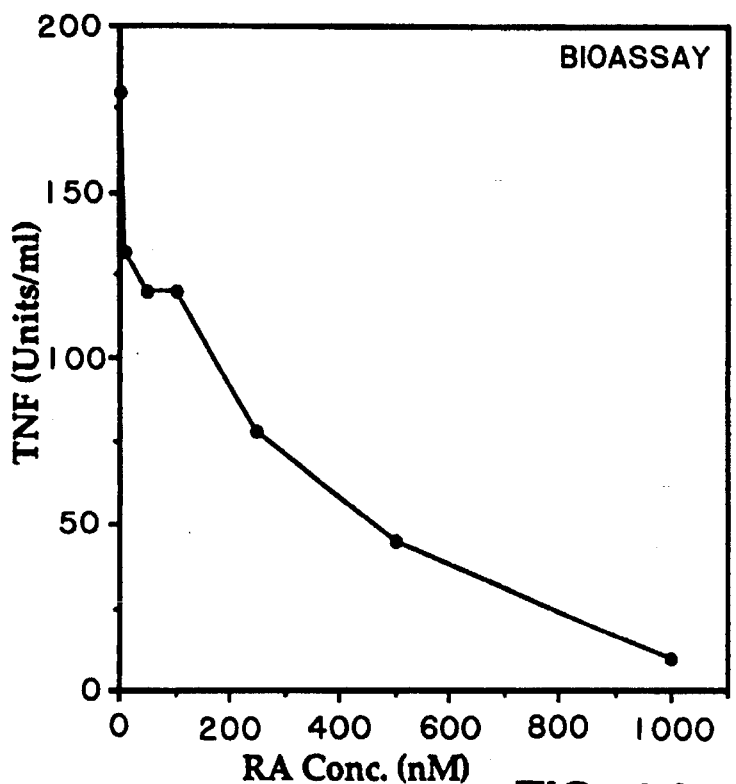
FIG. 2 shows the dose-dependent inhibition of TNF production by ATRA from peritoneal macrophages. Macrophage monolayers were activated by IFN-g+LPS in the presence of indicated ATRA dose levels. Four hour cell-free supernatants were analyzed for TNF either by using L929 cells as targets (FIG. 2A) or using murine TNF-specific enzyme linked immunoabsorbent assay (ELISA) kit (FIG. 2B) as described in Example 3. Results shown are average of quadruplicate values (±SD in B) from one of two experiments.
Figure 2B:
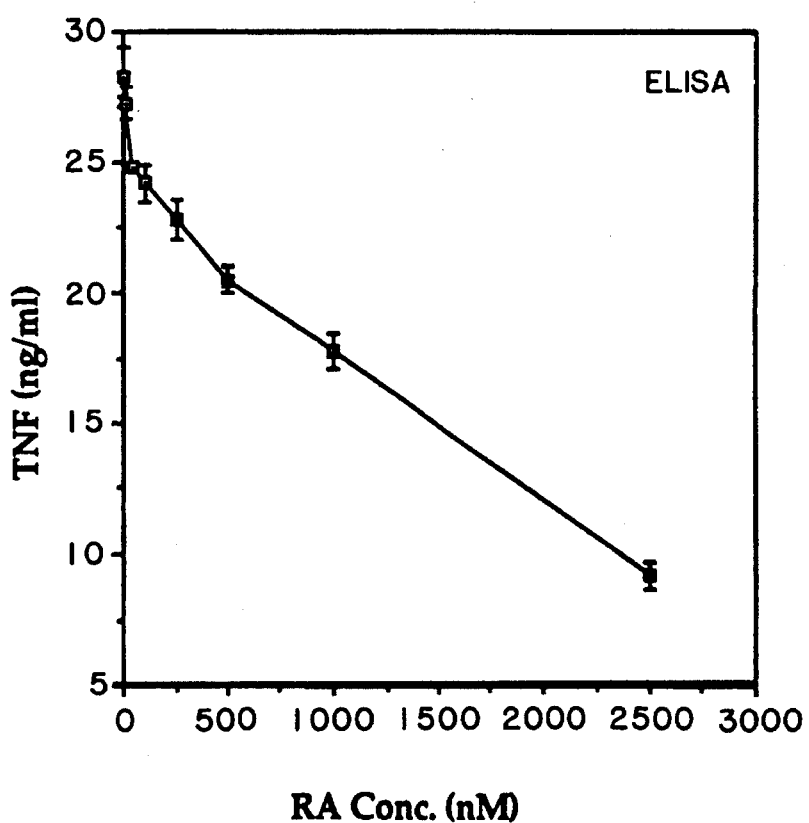

FIG. 2 demonstrates a dose-related inhibition of TNF secretion by ATRA. ATRA inhibited TNF secretion starting at $10^{-8}M$ and maximum inhibition was seen at $1-2.5\times10^{-6}M$. Similar results were obtained in two other independent experiments. In order to rule out the possibility that decreased TNF activity in ATRA-treated cultures was not due to the accelerated release of soluble TNF receptor, culture supernatants were subjected to ELISA for TNF protein determination. FIG. 2B clearly shows that the decrease in TNF activity was due to a decrease in TNF protein secretion. Furthermore, ATRA treated macrophages showed no alteration in binding to $^{125}$I-labelled TNF.

Figure 3A:
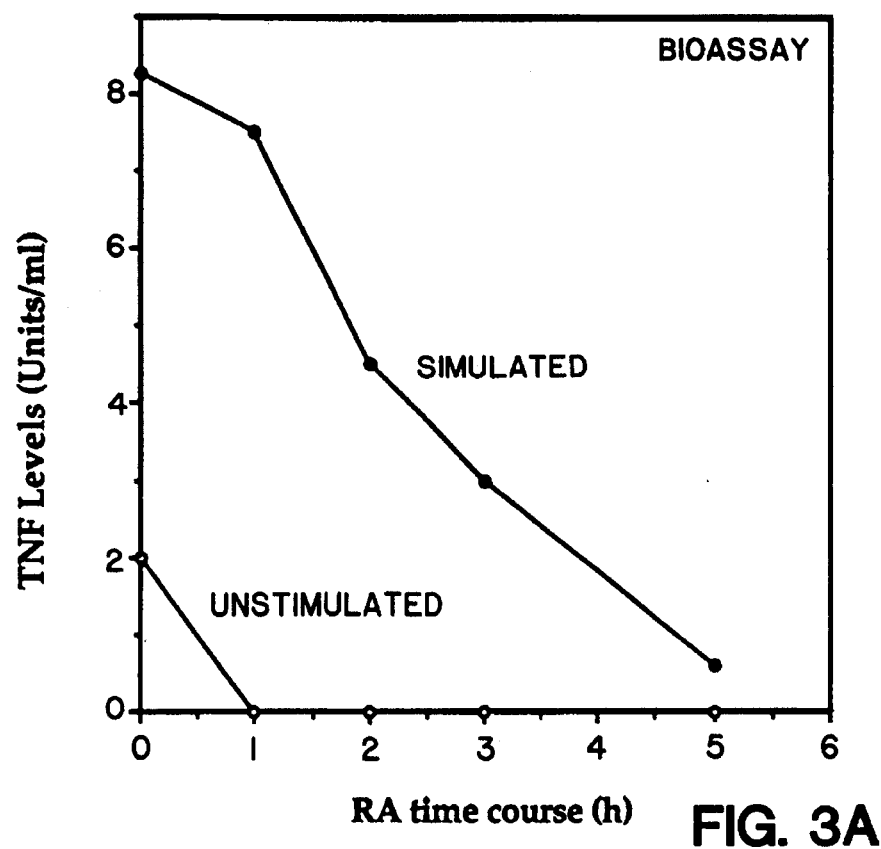
FIG. 3 shows the time-dependent inhibition of TNF production by ATRA from activated peritoneal macrophages. Macrophage monolayers were incubated for a total of 5 hours in presence of medium alone (0) or medium containing activators (IFN-g+LPS, ●). ATRA (1 µM) was added to different cultures at various times prior to harvesting the supernatants. Cell-free supernatants were then used to determine the TNF levels in a bioassay (FIG. 3A) or by ELISA (FIG. 3B). Results shown are an average of triplicate values form one of two experiments.
Figure 3B:
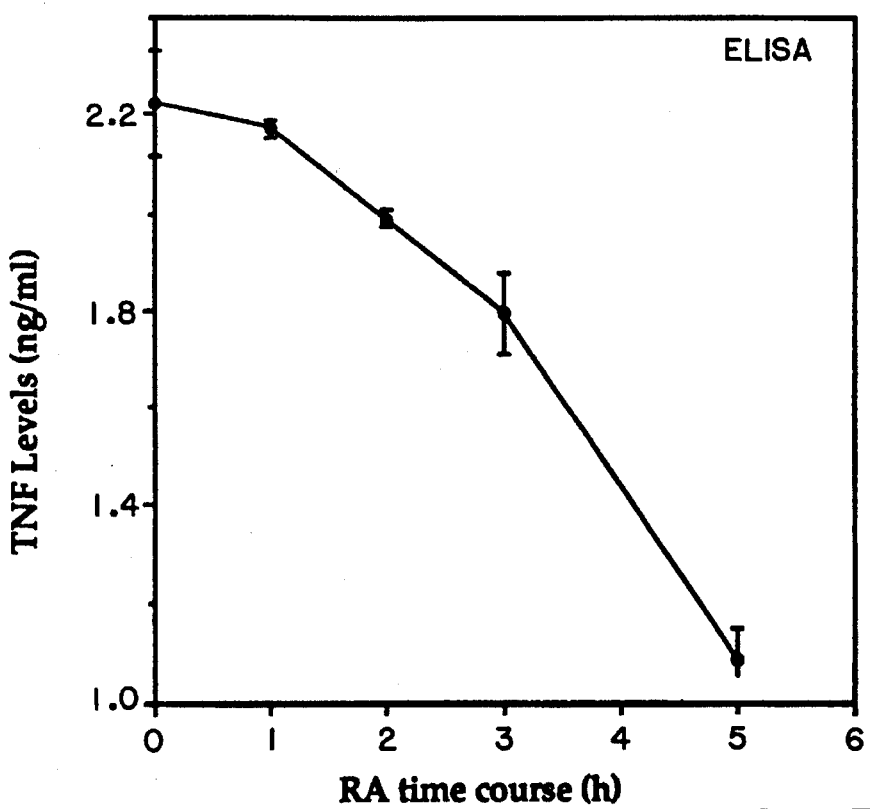

FIG. 3 illustrates that a continuous presence of ATRA throughout the culture period during the activation phase was essential for ATRA to exert maximal inhibition of TNF release by activated macrophages. Thus, inhibition of TNF production could be reached in a time-dependent manner by delaying addition of ATRA to the macrophage cultures, following initiation of their activation with IFN-γ and LPS.

EXAMPLE 6

Effect of ATRA in RAW 264.7 cells

Figure 4:
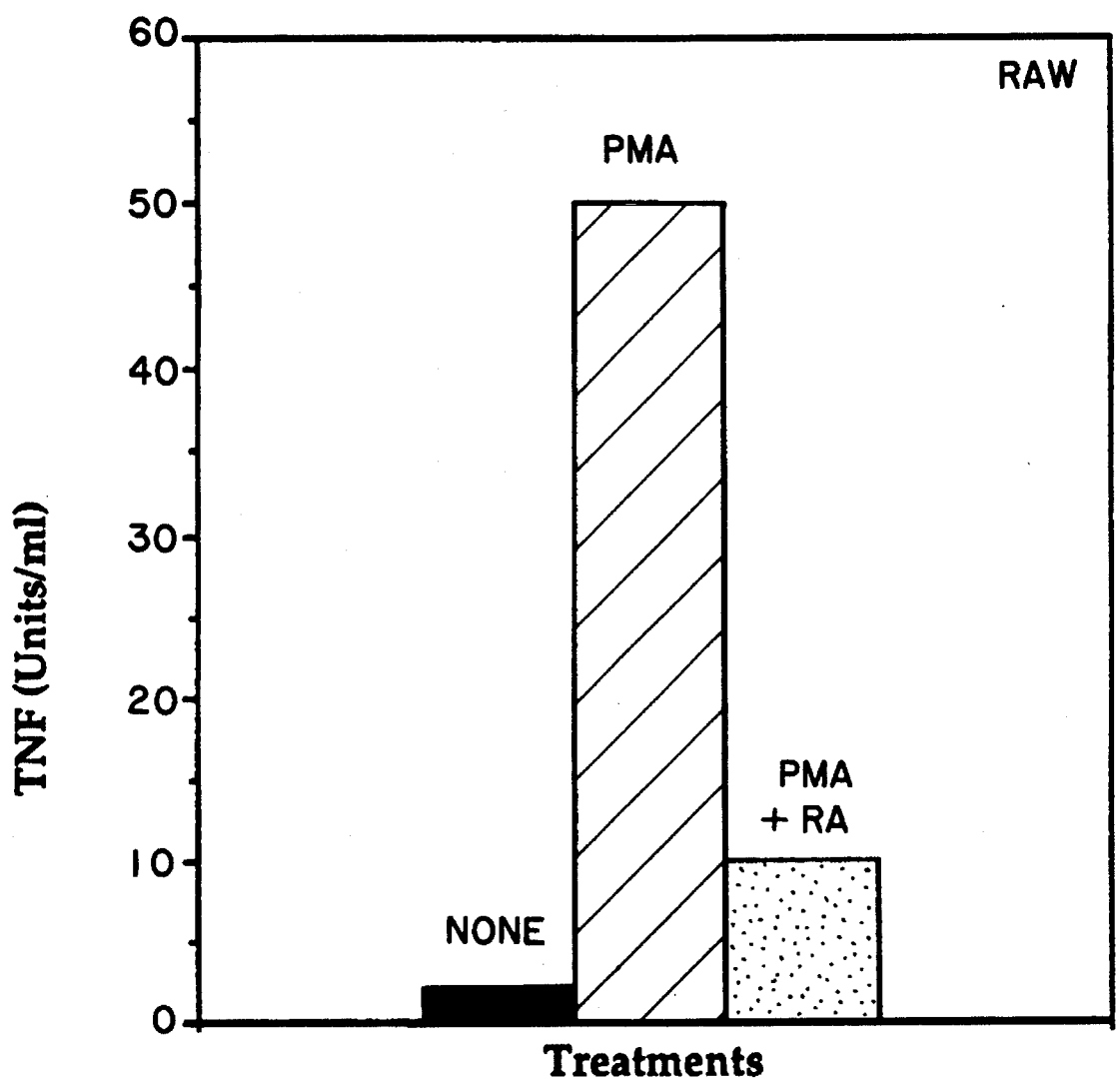
FIG. 4 shows the effect of ATRA-treatment on TNF production from RAW-264.7 cells. RAW 264.7 cells during exponential-phase of cell growth, were cultured in presence or absence of phorbol ester (TPA, 20 ng/ml) and/or ATRA (1 µM) in 24-well plates ($2 \times 10^6$ cells/well). Forty-eight hours later, cell-free supernatants were harvested and assayed for TNF activity. Results are an average of triplicate values form one of the three similar experiments.

Several transformed cell lines have been shown to produce TNF in response to their activation with tumor promoter phorbol ester (TPA). To ascertain whether ATRA-mediated suppression of TNF is a generalized phenomenon, RAW-264.7, a murine macrophage-like cell line, was examined for its ability to produce TNF in response to TPA (10 μg/ml) in presence and absence of ATRA (1 μM). FIG. 4 demonstrates that ATRA is a potent inhibitor of TPA-triggered TNF production in RAW-264.7 cells. The decrease in TNF activity in culture supernatants was associated with a parallel decrease in the amount of TNF protein as determined by murine-TNF specific ELISA kit.

EXAMPLE 7

Effect on ATRA on NO-production from activated macrophages

Figure 5:
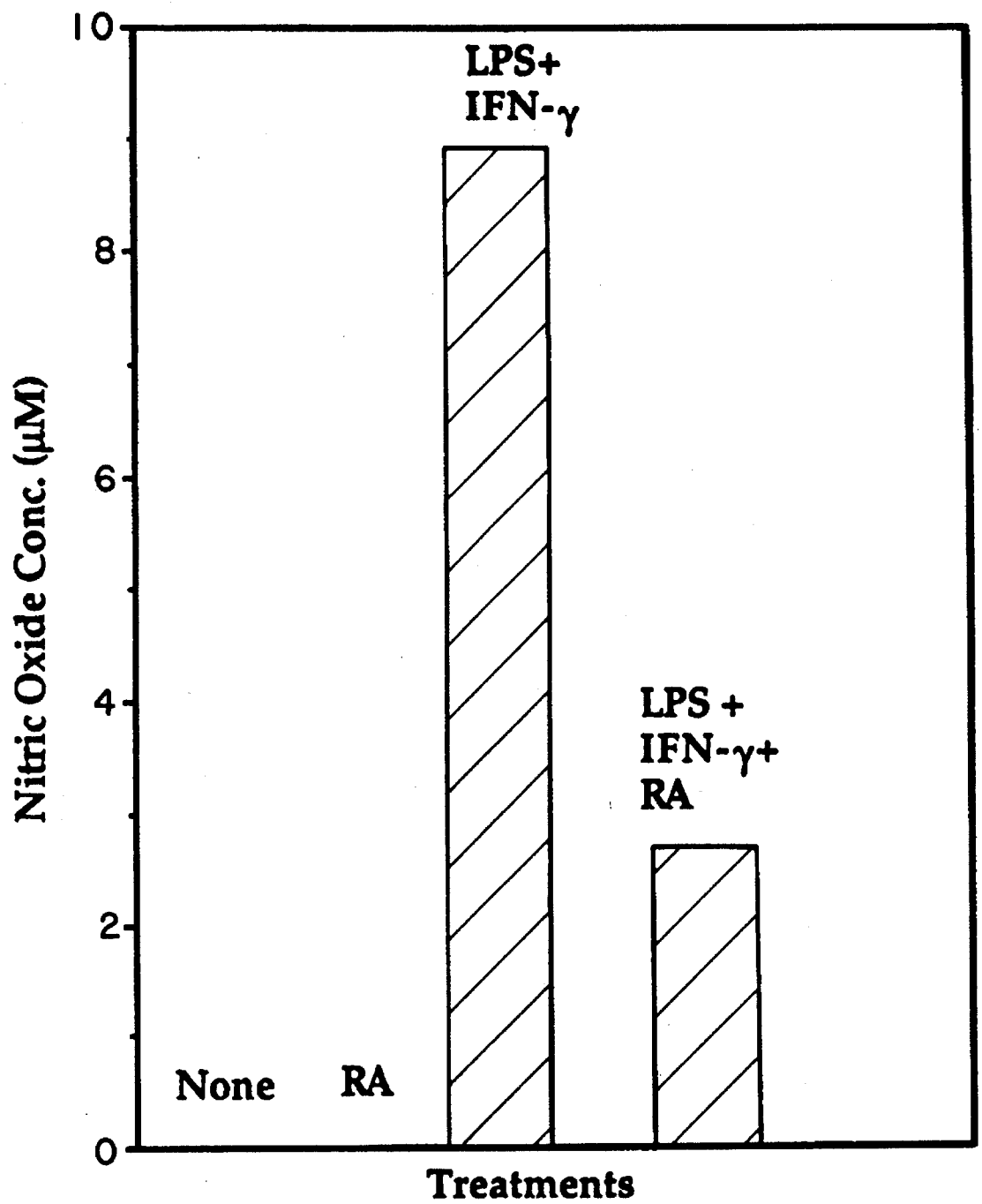
FIG. 5 shows the inhibition of NO production by ATRA from in vitro activated murine peritoneal macrophages. Two million cells were incubated in presence or absence of activators with or without 1 µM ATRA. Twenty-four hours later, cell-free supernatants were harvested and assayed for NO levels as described in Example 4. Results are an average of quadruplicate values from a representative experiment.
Figure 6A:
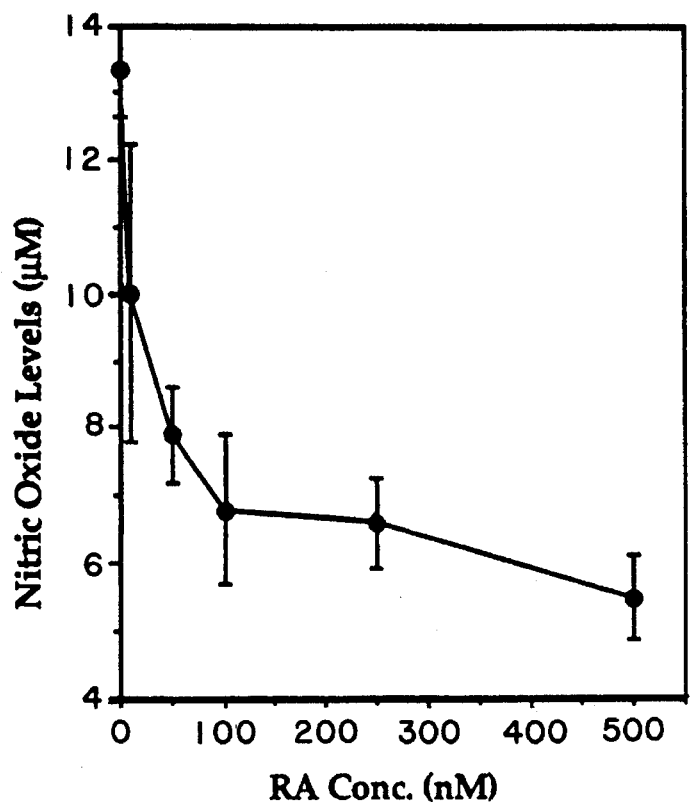
FIG. 6 shows the dose-dependent and time-dependent inhibition of NO production by ATRA from peritoneal macrophages. Macrophage monolayers were activated with IFN-g (10 U/ml) and LPS (100 ng/ml) along with ATRA at indicated dose levels (FIG. 6A). Alternatively, ATRA was added at various time intervals prior to harvesting the supernatants (FIG. 6B) after 24 hours of activation period. Cell-free supernatants were assayed for NO production. Results are an average of quadruplicate values ±SD.
Figure 6B:
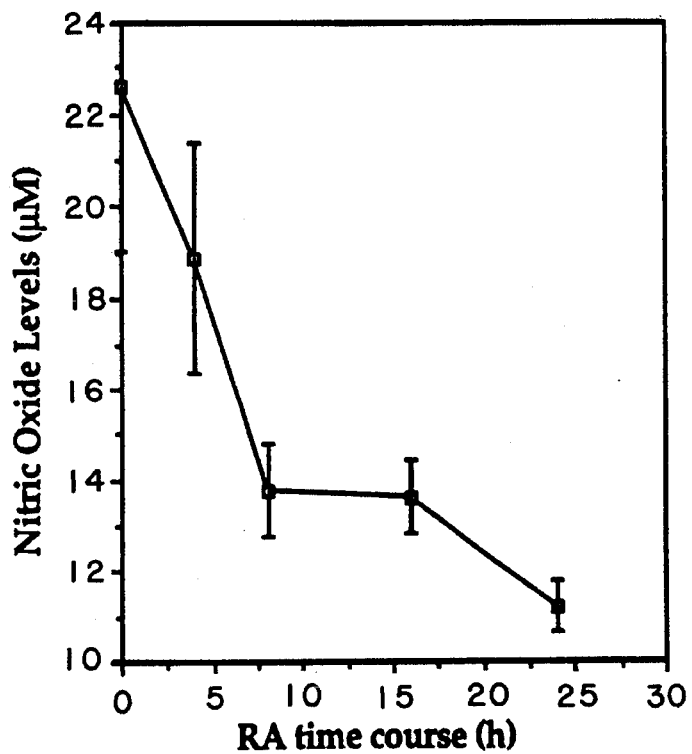

As shown in FIG. 5, activation of resident peritoneal mouse macrophages with IFN-γ and LPS in presence of ATRA, greatly decreased the NO— production in culture supernatants. The effect of ATRA on NO— production by activated macrophages was dose-dependent (FIG. 6A) and time-dependent (FIG. 6B). Thus, the inhibitory effect was evident at a physiological dose level of ATRA (10 nM) and became maximal at a pharmacologically achievable dose level (1 μM).

Similar to its effect on TNF production, continuous presence of ATRA was needed throughout the activation period in order to exert optimum inhibitory effect on NO production. Thus, addition of ATRA at various concentrations (FIG. 6A) and at various time intervals (FIG. 6B) after initiation of the activation with IFN-γ/LPS, showed a time-dependent increase in accumulation of NO- in the culture supernatants.

Macrophages play a critical role in host defense against infectious agents and tumors. They also participate in regulation of several immune functions, such as inflammatory responses. Most of these responses are modified through the production of soluble mediators called cytokines. The present invention describes the down regulatory effect of ATRA and its analogues (retinoids) on LPS/IFN-γ triggered in vitro production of TNF and NO— by mouse peritoneal macrophages. The suppression of TNF and NO was observed with as little dose of ATRA as 10 nM, a physiological concentration. The observed effects, therefore, are of physiological significance. The plasma concentration of ATRA can be achieved in micromolar levels following ATRA administration. At this concentration, 75% to 90% of TNF production was blocked by activated macrophages (FIG. 1).

TNF and NO— have both been shown to play a key role in macrophage-mediated inflammatory responses as well as in killing of tumor cells. Endogenous and exogenous retinoids (including ATRA) are potent inhibitors of activated macrophage-mediated cytostasis against murine adenocarcinoma (EMT-6) target cells. Arginine-dependent $NO_2/NO_3^-$ production by activated macrophages, on the other hand, has been shown to induce inhibition of mitochondrial respiration that eventually lead to growth inhibition of EMT-6 cells.

The observed inhibitory effect of ATRA on TNF and NO production were not due to their effect on prostaglandin production. ATRA, at applied concentrations, had no effect on prostaglandin E production by activated macrophages. Similarly, concentrations of ATRA (up to 2.5 µM) used in the methods of the present invention, showed no apparent toxic effects on cultured macrophages. TNF, in combination with other cytokines, such as IFN-γ is capable of inducing NO production by macrophages.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of inhibiting the production of nitric oxide, comprising the step of administering to an animal in need of such treatment a pharmacologically effective dose of a retinoic acid compound, wherein said animal has a pathophysiological state selected from the group consisting of sepsis, autoimmune diseases, cachexia, cerebral malaria and capillary leak syndrome.

2. The method of claim 1, wherein said retinoic acid compound is selected from the group consisting of all-trans-retinoic acid, 4-hydroxy-retinoic acid and 13-cis-retinoic acid.

3. The method of claim 1, wherein said animal is a human.

4. The method of claim 1, wherein said dose of said retinoic acid compound is from about 10 nM to about 1 µM.

5. A method of treating a pathophysiological state in an animal, wherein said state is characterized by production of an undesirable level of nitric oxide, comprising the step of administering a pharmacologically effective dose of a retinoic acid compound to said animal, wherein said pathophysiological state is selected from the group consisting of sepsis, autoimmune disease, cachexia, cerebral malaria and capillary leak syndrome.

6. The method of claim 5, wherein said retinoic acid compound is selected from the group consisting of all-trans-retinoic acid, 4-hydroxy-retinoic acid and 13-cis-retinoic acid.

7. The method of claim 5, wherein said animal is a human.

8. The method of claim 5, wherein said dose of said retinoic acid compound is from about 10 nM to about 1 µM.

9. The method of claim 5, wherein said autoimmune disease is selected from the group consisting of systemic lupus erythematosus, rheumatoid arthritis and multiple sclerosis.

* * * * *

UNITED STATES PATENT AND TRADEMARK OFFICE
CERTIFICATE OF CORRECTION

PATENT NO. : 5,457,129 Page 1 of 1
DATED : October 10, 1995
INVENTOR(S) : Bharat B. Aggarwal and Kapil Mehta It is certified that error appears in the above-identified patent and that said Letters Patent is hereby corrected as shown below:

Column 1:
Line 66, "flee-radical" should read --free-radical--.

Column 5:
Line 46, "frat bottomed" should read --flat bottomed--.

Column 6:
Line 43, "is" should read --was--.
Line 50, "Ding et al." should read --Ding, et al.,--
Line 67, "Mehta" should read --Metha,--.

Column 7:
Line 45, "Retinal" should read --Retinol--.

Signed and Sealed this

Nineteenth Day of June, 2001

*Attest:*

NICHOLAS P. GODICI
*Attesting Officer* Acting Director of the United States Patent and Trademark Office